US008865877B2

(12) United States Patent
Gross

(10) Patent No.: US 8,865,877 B2
(45) Date of Patent: Oct. 21, 2014

(54) COMPOSITIONS AND METHODS FOR SOLUBILIZING MEMBRANE PROTEINS WITHOUT THE USE OF DETERGENT

(75) Inventor: Adrian Gross, Evanston, IL (US)

(73) Assignee: Northwestern University, Evanston, IL (US)

( * ) Notice: Subject to any disclaimer, the term of this patent is extended or adjusted under 35 U.S.C. 154(b) by 276 days.

(21) Appl. No.: 13/052,876

(22) Filed: Mar. 21, 2011

(65) Prior Publication Data

US 2011/0230650 A1 Sep. 22, 2011

Related U.S. Application Data

(60) Provisional application No. 61/315,632, filed on Mar. 19, 2010.

(51) Int. Cl.
*A23J 1/10* (2006.01)
*C07K 1/10* (2006.01)

(52) U.S. Cl.
USPC ........................................................ 530/412

(58) Field of Classification Search
None
See application file for complete search history.

(56) References Cited

U.S. PATENT DOCUMENTS 7,048,949 B2 5/2006 Sligar et al.
7,083,958 B2 * 8/2006 Sligar et al. ................... 435/183

OTHER PUBLICATIONS

Bayburt et al., "Assembly of single bacteriorhodopsin trimers in bilayer nanodiscs", Archives of Biochemistry and Biophysics, 2006, 450:215-222.
Denisov et al., "Directed Self-Assembly of Monodisperse Phospholipid Bilayer Nanodiscs with Controlled Size", J. Am. Chem. Soc., 2004, 126:3477-3487.
Tatusova et al., "Blast 2 Sequences, a new tool for comparing protein and nucleotide sequences", FEMS Microbiology Letters, 1999, 174:247-250.

* cited by examiner

*Primary Examiner* — Gary Nickol
*Assistant Examiner* — Khatol Shahnan-Shah
(74) *Attorney, Agent, or Firm* — Andrus Intellectual Property Law, LLP

(57) ABSTRACT

Disclosed are compositions and methods for isolating proteins from lipids. The isolation methods may utilize derivatives of apolipoprotein A1 for isolating membrane proteins from membranes without the use of detergent.

16 Claims, 7 Drawing Sheets

?

13.2 ml 12.3 ml 12.0 ml

SEQUENCE LISTING

```
<160> NUMBER OF SEQ ID NOS: 7

<210> SEQ ID NO 1
<211> LENGTH: 55
<212> TYPE: PRT
<213> ORGANISM: Homo sapiens

<400> SEQUENCE: 1

Phe Gln Lys Lys Trp Gln Glu Glu Met Glu Leu Tyr Arg Gln Lys Val
1               5                   10                  15

Glu Pro Leu Arg Ala Glu Leu Gln Glu Gly Ala Arg Gln Lys Leu His
            20                  25                  30

Glu Leu Gln Glu Lys Leu Ser Pro Leu Gly Glu Glu Met Arg Asp Arg
        35                  40                  45

Ala Arg Ala His Val Asp Ala
    50                  55

<210> SEQ ID NO 2
<211> LENGTH: 24
<212> TYPE: PRT
<213> ORGANISM: Artificial
<220> FEATURE:
<223> OTHER INFORMATION: N-terminal sequence having a histidine tag

<400> SEQUENCE: 2

Met Gly His His His His His His Asp Tyr Asp Ile Pro Thr Thr
1               5                   10                  15

Glu Asn Leu Tyr Phe Gln Gly Ala
            20

<210> SEQ ID NO 3
<211> LENGTH: 190
<212> TYPE: PRT
<213> ORGANISM: Artificial
<220> FEATURE:
<223> OTHER INFORMATION: Trimer of truncated form of human chain A of
      apolipoprotein A-I having N-terminal sequence with histidine tag

<400> SEQUENCE: 3

Met Gly His His His His His His Asp Tyr Asp Ile Pro Thr Thr
1               5                   10                  15

Glu Asn Leu Tyr Phe Gln Gly Ala Phe Gln Lys Lys Trp Gln Glu Glu
            20                  25                  30

Met Glu Leu Tyr Arg Gln Lys Val Glu Pro Leu Arg Ala Glu Leu Gln
        35                  40                  45
```

Glu Gly Ala Arg Gln Lys Leu His Glu Leu Gln Glu Lys Leu Ser Pro
            50                  55                  60

Leu Gly Glu Glu Met Arg Asp Arg Ala Arg Ala His Val Asp Ala Phe
65                  70                  75                  80

Gln Lys Lys Trp Gln Glu Glu Met Glu Leu Tyr Arg Gln Lys Val Glu
                85                  90                  95

Pro Leu Arg Ala Glu Leu Gln Glu Gly Ala Arg Gln Lys Leu His Glu
            100                 105                 110

Leu Gln Glu Lys Leu Ser Pro Leu Gly Glu Glu Met Arg Asp Arg Ala
        115                 120                 125

Arg Ala His Val Asp Ala Phe Gln Lys Lys Trp Gln Glu Glu Met Glu
    130                 135                 140

Leu Tyr Arg Gln Lys Val Glu Pro Leu Arg Ala Glu Leu Gln Glu Gly
145                 150                 155                 160

Ala Arg Gln Lys Leu His Glu Leu Gln Glu Lys Leu Ser Pro Leu Gly
                165                 170                 175

Glu Glu Met Arg Asp Arg Ala Arg Ala His Val Asp Ala Ala
            180                 185                 190

<210> SEQ ID NO 4
<211> LENGTH: 245
<212> TYPE: PRT
<213> ORGANISM: Artificial
<220> FEATURE:
<223> OTHER INFORMATION: Tetramer of truncated form of human chain A of
      apolipoprotein A-I having N-terminal sequence with histidine tag

<400> SEQUENCE: 4

Met Gly His His His His His His Asp Tyr Asp Ile Pro Thr Thr
1               5                   10                  15

Glu Asn Leu Tyr Phe Gln Gly Ala Phe Gln Lys Lys Trp Gln Glu Glu
            20                  25                  30

Met Glu Leu Tyr Arg Gln Lys Val Glu Pro Leu Arg Ala Glu Leu Gln
        35                  40                  45

Glu Gly Ala Arg Gln Lys Leu His Glu Leu Gln Glu Lys Leu Ser Pro
            50                  55                  60

Leu Gly Glu Glu Met Arg Asp Arg Ala Arg Ala His Val Asp Ala Phe
65                  70                  75                  80

Gln Lys Lys Trp Gln Glu Glu Met Glu Leu Tyr Arg Gln Lys Val Glu
                85                  90                  95

Pro Leu Arg Ala Glu Leu Gln Glu Gly Ala Arg Gln Lys Leu His Glu
            100                 105                 110

Leu Gln Glu Lys Leu Ser Pro Leu Gly Glu Glu Met Arg Asp Arg Ala
        115                 120                 125

Arg Ala His Val Asp Ala Phe Gln Lys Lys Trp Gln Glu Glu Met Glu
    130                 135                 140

Leu Tyr Arg Gln Lys Val Glu Pro Leu Arg Ala Glu Leu Gln Glu Gly
145                 150                 155                 160

Ala Arg Gln Lys Leu His Glu Leu Gln Glu Lys Leu Ser Pro Leu Gly
                165                 170                 175

Glu Glu Met Arg Asp Arg Ala Arg Ala His Val Asp Ala Phe Gln Lys
            180                 185                 190

Lys Trp Gln Glu Glu Met Glu Leu Tyr Arg Gln Lys Val Glu Pro Leu
        195                 200                 205

Arg Ala Glu Leu Gln Glu Gly Ala Arg Gln Lys Leu His Glu Leu Gln
210                 215                 220

```
Glu Lys Leu Ser Pro Leu Gly Glu Glu Met Arg Asp Arg Ala Arg Ala
225                 230                 235                 240

His Val Asp Ala Ala
                245

<210> SEQ ID NO 5
<211> LENGTH: 300
<212> TYPE: PRT
<213> ORGANISM: Artificial
<220> FEATURE:
<223> OTHER INFORMATION: Pentamer of truncated form of human chain A of
      apolipoprotein A-I having N-terminal histidine tag

<400> SEQUENCE: 5

Met Gly His His His His His His Asp Tyr Asp Ile Pro Thr Thr
1               5                   10                  15

Glu Asn Leu Tyr Phe Gln Gly Ala Phe Gln Lys Lys Trp Gln Glu
                20                  25                  30

Met Glu Leu Tyr Arg Gln Lys Val Glu Pro Leu Arg Ala Glu Leu Gln
                35                  40                  45

Glu Gly Ala Arg Gln Lys Leu His Glu Leu Gln Glu Lys Leu Ser Pro
50                  55                  60

Leu Gly Glu Glu Met Arg Asp Arg Ala Arg Ala His Val Asp Ala Phe
65                  70                  75                  80

Gln Lys Lys Trp Gln Glu Met Glu Leu Tyr Arg Gln Lys Val Glu
                85                  90                  95

Pro Leu Arg Ala Glu Leu Gln Glu Gly Ala Arg Gln Lys Leu His Glu
                100                 105                 110

Leu Gln Glu Lys Leu Ser Pro Leu Gly Glu Glu Met Arg Asp Arg Ala
                115                 120                 125

Arg Ala His Val Asp Ala Phe Gln Lys Lys Trp Gln Glu Glu Met Glu
        130                 135                 140

Leu Tyr Arg Gln Lys Val Glu Pro Leu Arg Ala Glu Leu Gln Glu Gly
145                 150                 155                 160

Ala Arg Gln Lys Leu His Glu Leu Gln Glu Lys Leu Ser Pro Leu Gly
                165                 170                 175

Glu Glu Met Arg Asp Arg Ala Arg Ala His Val Asp Ala Phe Gln Lys
                180                 185                 190

Lys Trp Gln Glu Glu Met Glu Leu Tyr Arg Gln Lys Val Glu Pro Leu
                195                 200                 205

Arg Ala Glu Leu Gln Glu Gly Ala Arg Gln Lys Leu His Glu Leu Gln
210                 215                 220

Glu Lys Leu Ser Pro Leu Gly Glu Glu Met Arg Asp Arg Ala Arg Ala
225                 230                 235                 240

His Val Asp Ala Phe Gln Lys Lys Trp Gln Glu Glu Met Glu Leu Tyr
                245                 250                 255

Arg Gln Lys Val Glu Pro Leu Arg Ala Glu Leu Gln Glu Gly Ala Arg
                260                 265                 270

Gln Lys Leu His Glu Leu Gln Glu Lys Leu Ser Pro Leu Gly Glu Glu
        275                 280                 285

Met Arg Asp Arg Ala Arg Ala His Val Asp Ala Ala
        290                 295                 300

<210> SEQ ID NO 6
<211> LENGTH: 355
<212> TYPE: PRT
```

<213> ORGANISM: Artificial
<220> FEATURE:
<223> OTHER INFORMATION: Hexamer of truncated form of human chain A of apolipoprotein A-I having a N-terminal histidine tag

<400> SEQUENCE: 6

```
Met Gly His His His His His His Asp Tyr Asp Ile Pro Thr Thr
1               5                   10                  15

Glu Asn Leu Tyr Phe Gln Gly Ala Phe Gln Lys Lys Trp Gln Glu
                20                  25                  30

Met Glu Leu Tyr Arg Gln Lys Val Glu Pro Leu Arg Ala Glu Leu Gln
            35                  40                  45

Glu Gly Ala Arg Gln Lys Leu His Glu Leu Gln Glu Lys Leu Ser Pro
    50                  55                  60

Leu Gly Glu Glu Met Arg Asp Arg Ala Arg Ala His Val Asp Ala Phe
65                  70                  75                  80

Gln Lys Lys Trp Gln Glu Glu Met Glu Leu Tyr Arg Gln Lys Val Glu
                85                  90                  95

Pro Leu Arg Ala Glu Leu Gln Glu Gly Ala Arg Gln Lys Leu His Glu
                100                 105                 110

Leu Gln Glu Lys Leu Ser Pro Leu Gly Glu Glu Met Arg Asp Arg Ala
            115                 120                 125

Arg Ala His Val Asp Ala Phe Gln Lys Lys Trp Gln Glu Glu Met Glu
        130                 135                 140

Leu Tyr Arg Gln Lys Val Glu Pro Leu Arg Ala Glu Leu Gln Glu Gly
145                 150                 155                 160

Ala Arg Gln Lys Leu His Glu Leu Gln Glu Lys Leu Ser Pro Leu Gly
                165                 170                 175

Glu Glu Met Arg Asp Arg Ala Arg Ala His Val Asp Ala Phe Gln Lys
                180                 185                 190

Lys Trp Gln Glu Glu Met Glu Leu Tyr Arg Gln Lys Val Glu Pro Leu
            195                 200                 205

Arg Ala Glu Leu Gln Glu Gly Ala Arg Gln Lys Leu His Glu Leu Gln
        210                 215                 220

Glu Lys Leu Ser Pro Leu Gly Glu Glu Met Arg Asp Arg Ala Arg Ala
225                 230                 235                 240

His Val Asp Ala Phe Gln Lys Lys Trp Gln Glu Glu Met Glu Leu Tyr
                245                 250                 255

Arg Gln Lys Val Glu Pro Leu Arg Ala Glu Leu Gln Glu Gly Ala Arg
                260                 265                 270

Gln Lys Leu His Glu Leu Gln Glu Lys Leu Ser Pro Leu Gly Glu Glu
            275                 280                 285

Met Arg Asp Arg Ala Arg Ala His Val Asp Ala Phe Gln Lys Lys Trp
290                 295                 300

Gln Glu Glu Met Glu Leu Tyr Arg Gln Lys Val Glu Pro Leu Arg Ala
305                 310                 315                 320

Glu Leu Gln Glu Gly Ala Arg Gln Lys Leu His Glu Leu Gln Glu Lys
                325                 330                 335

Leu Ser Pro Leu Gly Glu Glu Met Arg Asp Arg Ala Arg Ala His Val
            340                 345                 350

Asp Ala Ala
        355
```

<210> SEQ ID NO 7
<211> LENGTH: 201

```
<212> TYPE: PRT
<213> ORGANISM: Homo sapiens

<400> SEQUENCE: 7

Met Leu Lys Leu Leu Asp Asn Trp Asp Ser Val Thr Ser Thr Phe Ser
1               5                   10                  15

Lys Leu Arg Glu Gln Leu Gly Pro Val Thr Gln Glu Phe Trp Asp Asn
                20                  25                  30

Leu Glu Lys Glu Thr Glu Gly Leu Arg Gln Glu Met Ser Lys Asp Leu
            35                  40                  45

Glu Glu Val Lys Ala Lys Val Gln Pro Tyr Leu Asp Asp Phe Gln Lys
        50                  55                  60

Lys Trp Gln Glu Glu Met Glu Leu Tyr Arg Gln Lys Val Glu Pro Leu
65                      70                  75                  80

Arg Ala Glu Leu Gln Glu Gly Ala Arg Gln Lys Leu His Glu Leu Gln
                85                  90                  95

Glu Lys Leu Ser Pro Leu Gly Glu Glu Met Arg Asp Arg Ala Arg Ala
                100                 105                 110

His Val Asp Ala Leu Arg Thr His Leu Ala Pro Tyr Ser Asp Glu Leu
            115                 120                 125

Arg Gln Arg Leu Ala Ala Arg Leu Glu Ala Leu Lys Glu Asn Gly Gly
        130                 135                 140

Ala Arg Leu Ala Glu Tyr His Ala Lys Ala Thr Glu His Leu Ser Thr
145                 150                 155                 160

Leu Ser Glu Lys Ala Lys Pro Ala Leu Glu Asp Leu Arg Gln Gly Leu
                165                 170                 175

Leu Pro Val Leu Glu Ser Phe Lys Val Ser Phe Leu Ser Ala Leu Glu
                180                 185                 190

Glu Tyr Thr Lys Lys Leu Asn Thr Gln
                195                 200
```

COMPOSITIONS AND METHODS FOR SOLUBILIZING MEMBRANE PROTEINS WITHOUT THE USE OF DETERGENT

CROSS-REFERENCE TO RELATED APPLICATIONS

This application claims the benefit under 35 U.S.C. §119 (e) to U.S. Provisional Application No. 61/315,632, filed on Mar. 19, 2010, the contents of which are incorporated herein by reference in their entirety.

STATEMENT REGARDING FEDERALLY SPONSORED RESEARCH OR DEVELOPMENT

This invention was made with government support under grant number GM058568 awarded by the National Institutes of Health (NIGMS). The government has certain rights in the invention.

FIELD

The field of the invention relates to compositions and methods for the isolation of proteins from associated lipids without the use of a detergent.

BACKGROUND

Membrane proteins perform many important biological functions, are targets of key clinical drugs, and make up nearly a third of the human proteome. Despite their prominence and importance, membrane proteins still account for only a small fraction of known protein structures. The reasons for this discrepancy are numerous, but can be summarized by stating that membrane proteins present many difficulties, including expression, purification, and crystallization. At the core of these difficulties lies the interaction between protein and lipid, the defining characteristic of a membrane protein. The isolation of membrane proteins usually requires that they be removed from the membrane by detergent solubilization, a process that often disrupts the native protein-lipid interaction and can lead to non-native protein conformations. Better tools to handle membrane proteins are needed.

SUMMARY

Disclosed are compositions and methods for isolating proteins from lipids. The isolation methods may include isolating membrane proteins from membranes without the use of detergent.

The isolation methods may utilize a composition comprising apolipoprotein A1 or a polypeptide derived from apolipoprotein A1 (SEQ ID NO:7), such as a variant, mutant, or truncated version of apolipoprotein A1 (i.e., a fragment of apolipoprotein A1). For example, the polypeptide may comprise at least 3, 4, 5, or 6 tandem repeats of a derivative of apolipoprotein A1 (e.g., a derivative comprising N-terminal and/or C-terminal truncations relative to SEQ ID NO:7). In some embodiments, the polypeptide utilized in the methods has a formula (SEQ ID NO:1)$_n$, where "n" is 3-6. The polypeptide having SEQ ID NO:1 includes an N-terminal truncation and a C-terminal truncation relative to apolipoprotein A1 (SEQ ID NO:7). Suitable polypeptides for the isolation methods may include, but are not limited to, polypeptides of SEQ ID NO:3 (comprising 3 tandem repeats of the derivative of apolipoprotein A1), SEQ ID NO:4 (comprising 4 tandem repeats of the derivative of apolipoprotein A1), SEQ ID NO:5 (comprising 5 tandem repeats of the derivative of apolipoprotein A1), and SEQ ID NO:6 (comprising 6 tandem repeats of the derivative of apolipoprotein A1). Preferably, the polypeptide utilized in the isolation methods comprises at least 4 tandem repeats of the derivative of apolipoprotein A1.

The polypeptide utilized in the isolation methods may comprise an N-terminal amino acid sequence having a peptide tag (e.g., a histidine tag having at least 6 consecutive histidine residues.) For example, the polypeptide utilized in the isolation methods may comprise an amino acid sequence: $N_{ter}$-(SEQ ID NO:1)$_n$, wherein "$N_{ter}$" is an amino acid sequence comprising a stretch of at least six histidine residues. The polypeptide utilized in the isolation methods may comprise an N-terminal amino acid sequence having a protease recognition sequence. For example, "$N_{ter}$" further may comprise a protease recognition sequence that is positioned C-terminal to the stretch of histidine residues. In some embodiments, "$N_{ter}$" may comprise SEQ ID NO:2.

In some embodiments, the polypeptide utilized in the isolation methods comprises an amino acid sequence: (LP)$_n$, wherein n is 3-6 and LP is an amino acid sequence having at least about 95% sequence identity to SEQ ID NO:1. Preferably, "n" is at least 4 and the polypeptide forms a holo-form nanodisc.

The aforementioned polypeptides may be utilized in methods for isolating proteins from lipids. In some embodiments, the isolation methods include (a) reacting a mixture comprising: (1) a protein associated with lipids (e.g., a membrane protein present in a membrane); and (2) any of the aforementioned polypeptides comprising tandem repeats of the derivatives of apolipoprotein A1; and (b) isolating the protein from the lipids (e.g., isolating the membrane protein from the membrane). Typically, the methods do not utilize detergent in order to isolate the proteins from the lipids. As such, typically the mixture does not include a detergent such as a nonionic detergent. The isolated protein typically may be present in a phospholipid membrane (e.g., a phospholipid bilayer).

DETAILED DESCRIPTION

Figure 1:
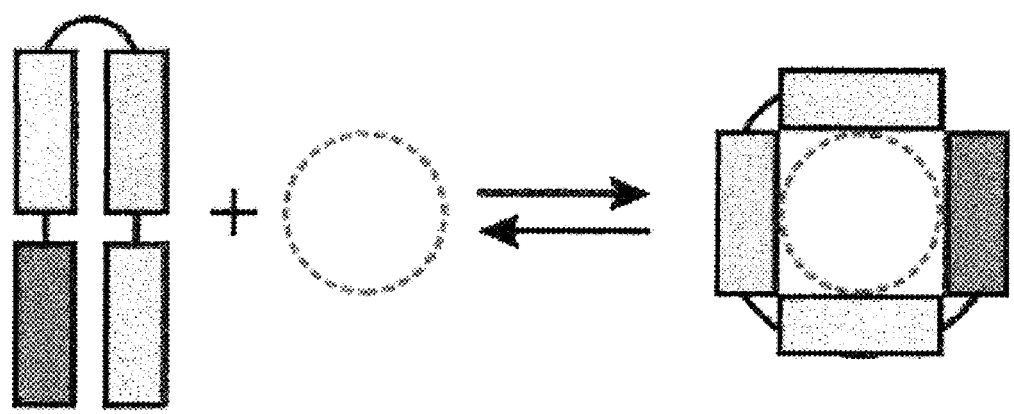
FIG. 1. illustrates nanodisc tools of the prior art and nanodisc tools as disclosed herein. Top: nanodisc technology of the prior art. The scaffolding protein can exist in both apo-form (left) and holo-form (nanodisc, right) (i.e., the two forms are in equilibrium (arrows)). To kinetically trap the nanodisc, the scaffolding protein and the necessary lipids are first mixed in detergent micelles and the nanodisc containing a bilayer (dashed circle) is formed by detergent removal. Bottom: nanodisc technology as presently disclosed. The scaffolding protein can exist only in the holo-form (no back arrow).
Figure 1:
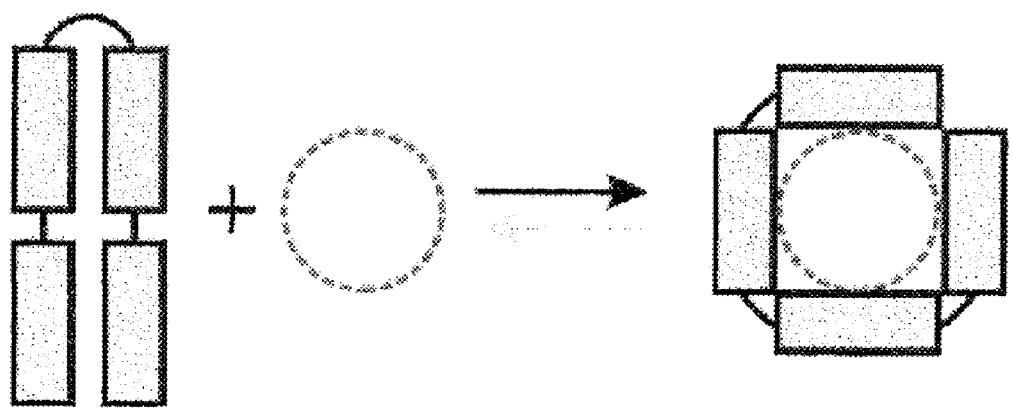

Disclosed are compositions and methods for isolating proteins from associated lipids. In some embodiments, the disclosed compositions may include polypeptides that are used to solubilize membrane protein complexes without the use of detergents. These polypeptides maintain the critical protein-lipid interactions and thus maintain the native structure of the complex. The disclosed subject matter further may be described utilizing terms as defined below.

Unless otherwise specified or indicated by context, the terms "a", "an", and "the" mean "one or more." For example, "a nanodisc" should be interpreted to mean "one or more nanodiscs."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising."

The terms peptide and polypeptide refer to polymers of amino acid residues. The peptides and polypeptides disclosed herein may be described via their "amino acid sequence." As used herein, the term "amino acid sequence" refers to amino acid residues joined by amide linkages. The term "amino acid residue," includes but is not limited to amino acid residues contained in the group consisting of alanine (Ala or A), cysteine (Cys or C), aspartic acid (Asp or D), glutamic acid (Glu or E), phenylalanine (Phe or F), glycine (Gly or G), histidine (His or H), isoleucine (Ile or I), lysine (Lys or K), leucine (Leu or L), methionine (Met or M), asparagine (Asn or N), proline (Pro or P), glutamine (Gln or Q), arginine (Arg or R), serine (Ser or S), threonine (Thr or T), valine (Val or V), tryptophan (Trp or W), and tyrosine (Tyr or Y) residues. The term "amino acid residue" also may include amino acid residues contained in the group consisting of homocysteine, 2-Aminoadipic acid, N-Ethylasparagine, 3-Aminoadipic acid, Hydroxylysine, β-alanine, β-Amino-propionic acid, allo-Hydroxylysine acid, 2-Aminobutyric acid, 3-Hydroxyproline, 4-Aminobutyric acid, 4-Hydroxyproline, piperidinic acid, 6-Aminocaproic acid, Isodesmosine, 2-Aminoheptanoic acid, allo-Isoleucine, 2-Aminoisobutyric acid, N-Methylglycine, sarcosine, 3-Aminoisobutyric acid, N-Methylisoleucine, 2-Aminopimelic acid, 6-N-Methyllysine, 2,4-Diaminobutyric acid, N-Methylvaline, Desmosine, Norvaline, 2,2'-Diaminopimelic acid, Norleucine, 2,3-Diaminopropionic acid, Ornithine, and N-Ethylglycine.

The terms "peptide" and "polypeptide" (and/or "protein") may be used interchangeably herein. However, generally a peptide is defined as a short polymer of amino acids, of a length typically of 20 or less amino acids, and more typically of a length of 12 or less amino acids (Garrett & Grisham, Biochemistry, $2^{nd}$ edition, 1999, Brooks/Cole, 110). In some embodiments, a peptide as contemplated herein may include no more than about 2, 3, 4, 5, 6, 7, 8, 9, 10, 11, 12, 13, 14, 15, 16, 17, 18, 19, or 20 amino acids. A polypeptide, also referred to as a protein, is typically of length ≥100 amino acids (Garrett & Grisham, Biochemistry, $2^{nd}$ edition, 1999, Brooks/Cole, 110). A polypeptide, as contemplated herein, may comprise, but is not limited to, 100, 101, 102, 103, 104, 105, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, about 1100, about 1200, about 1300, about 1400, about 1500, about 1750, about 2000, about 2250, about 2500 or more amino acid residues. A "protein" generally refers to a polypeptide (or peptide), which optionally may be further modified to include non-amino acid moieties and which exhibits a biological function.

The peptides and polypeptides contemplated herein may be further modified to include non-amino acid moieties. Modifications may include but are not limited to acylation (e.g., O-acylation (esters), N-acylation (amides), S-acylation (thioesters)), acetylation (e.g., the addition of an acetyl group, either at the N-terminus of the protein or at lysine residues), formylation lipoylation (e.g., attachment of a lipoate, a C8 functional group), myristoylation (e.g., attachment of myristate, a C14 saturated acid), palmitoylation (e.g., attachment of palmitate, a C16 saturated acid), alkylation (e.g., the addition of an alkyl group, such as an methyl at a lysine or arginine residue), isoprenylation or prenylation (e.g., the addition of an isoprenoid group such as farnesol or geranylgeraniol), amidation at C-terminus, glycosylation (e.g., the addition of a glycosyl group to either asparagine, hydroxylysine, serine, or threonine, resulting in a glycoprotein), Distinct from glycation, which is regarded as a nonenzymatic attachment of sugars, polysialylation (e.g., the addition of polysialic acid), glypiation (e.g., glycosylphosphatidylinositol (GPI) anchor formation, hydroxylation, iodination (e.g., of thyroid hormones), and phosphorylation (e.g., the addition of a phosphate group, usually to serine, tyrosine, threonine or histidine).

As used herein, a "variant" or "mutant" refers to a polypeptide or a peptide molecule having an amino acid sequence, respectively, that differs from a reference polypeptide or peptide. A variant or mutant may have one or more insertions, deletions, or substitutions of one or more amino acid residues relative to a reference molecule. A variant or mutant may include a truncated form or fragment of a reference polypeptide. For example, an apolipoprotein A1 variant polypeptide has one or more insertions, deletions, or substitutions of one or more one amino acid residues relative to the apolipoprotein A1 polypeptide.

As described herein, variants, mutants, truncated forms, or fragments (e.g., a apolipoprotein A1 variant, mutant, truncated form, or fragment polypeptide) may have 99%, 98%, 97%, 96%, 95%, 94%, 93%, 92%, 91%, 90%, 80%, 70%, 60%, or 50% amino acid sequence identity relative to a reference molecule (e.g., the apolipoprotein A1 polypeptide).

"Percentage sequence identity" may be determined by aligning two sequences using the Basic Local Alignment Search Tool available at the NBCI website (i.e., "b12seq" as described in Tatiana A. Tatusova, Thomas L. Madden (1999), "Blast 2 sequences—a new tool for comparing protein and nucleotide sequences", FEMS Microbiol Lett. 174:247-250, incorporated herein by reference in its entirety)). The variants, mutants, truncated forms, or fragments described herein may have one or functional or biological activities exhibited by a reference polypeptide (e.g., one or more functional or biological activities exhibited by apolipoprotein A1, including, but not limited to forming a holo-form nanodisc, and solubilizing membrane proteins).

As disclosed herein, a truncated form or fragment comprises or consists of a contiguous portion of an amino acid sequence of a full-length polypeptide. For example, a truncated form or fragment may lack a portion of the N-terminal sequence, the C-terminal sequence, or both terminal sequences of a full-length polypeptide. For example, a truncated-form or fragment of a full-length polypeptide may lack at least about a 10, 15, 20, 25, 30, 35, 40, 45, 50, 55, 60, 65, 70, 75, 80, 85, 90, 95, or 100 contiguous amino acid sequence of the N-terminal sequence, the C-terminal sequence, or both terminal sequences of the full-length polypeptide. In another example, a truncated form or fragment of a full-length polypeptide may comprise or consist of a 10, 15, 20, 25, 30, 35, 40, 45, 50, 55, 60, 65, 70, 75, 80, 85, 90, 95, or 100 contiguous amino acid sequence of the full-length polypeptide.

ILLUSTRATIVE EMBODIMENTS AND EXAMPLES

The following embodiments and examples are illustrative and are not intended to limit the scope of the claimed subject matter.

Embodiment 1. A polypeptide comprising an amino acid sequence: (SEQ ID NO:1)$_n$, wherein n is 3-6.

Embodiment 2. The polypeptide of embodiment 1, wherein n is 3.3.

Embodiment 3. The polypeptide of embodiment 1, wherein n is 4.

Embodiment 4. The polypeptide of embodiment 1, wherein n is 5.

Embodiment 5. The polypeptide of embodiment 1, wherein n is 6.

Embodiment 6. The polypeptide of embodiment 1, comprising an amino acid sequence: $N_{ter}$-(SEQ ID NO:1)$_n$, wherein $N_{ter}$ is an amino acid sequence comprising a stretch of at least six histidine residues.

Embodiment 7. The polypeptide of embodiment 6, wherein $N_{ter}$ further comprises a protease recognition sequence that is positioned C-terminal to the stretch of histidine residues.

Embodiment 8. The polypeptide of embodiment 6, wherein $N_{ter}$ comprises SEQ ID NO:2.

Embodiment 9. The polypeptide of embodiment 1, comprising SEQ ID NO:3.

Embodiment 10. The polypeptide of embodiment 1, comprising SEQ ID NO:4.

Embodiment 11. The polypeptide of embodiment 1, comprising SEQ ID NO:5.

Embodiment 12. The polypeptide of embodiment 1, comprising SEQ ID NO:6.

Embodiment 13. A polypeptide comprising an amino acid sequence: (LP)$_n$, wherein n is 3-6 and LP is an amino acid sequence having at least about 95% sequence identity to SEQ ID NO:1 and the polypeptide forms a holo-form nanodisc.

Embodiment 14. The polypeptide of embodiment 13, wherein n is 4.

Embodiment 15. The polypeptide of embodiment 13, wherein n is 5.

Embodiment 16. A method comprising: (a) reacting a mixture comprising: (1) a membrane protein present in a membrane; and (2) the polypeptide of any of embodiments 1-15; and (b) isolating the membrane protein from the membrane.

Embodiment 17. The method of embodiment 16, wherein the mixture does not comprise detergent.

Embodiment 18. The method of embodiment 16, wherein the mixture does not comprise a nonionic detergent.

Embodiment 19. The method of any of embodiments 16-18, wherein the membrane comprises phospholipids.

Embodiment 20. The method of any of embodiments 16-19, wherein the membrane is a phospholipid bilayer.

Some embodiments of the polypeptides are based on, but not limited to apolipoprotein A1, which is a scaffolding protein that can shuttle back and forth between an empty apo-form and a membrane-loaded holo-form. Examples of similar polypeptide based on apolipoprotein A1 are known in the art and have been described before (Denisov, I. G., et. al. 2004, *J Am Chem Sac* 126, 3477-3487, the content of which is incorporated herein by reference in its entirety). In conventional "nanodisc" technology, detergent-solubilized scaffolding protein (e.g., a truncated form of apolipoprotein A1), detergent-solubilized membrane protein, and detergent-solubilized lipid are combined to form a mixture. Detergent is removed from the mixture, and "nanodiscs" containing a lipid bilayer with embedded membrane protein are formed (FIG. 1, top).

In the methods disclosed herein, a different approach is utilized. Polypeptide derivatives of a scaffolding protein having altered energetics between the two states (i.e., holo-form versus apo-form) are utilized. The polypeptides utilized in the disclosed methods spontaneously engulf patches of native lipids and render them water soluble (FIG. 1, bottom). Accordingly, the polypeptide derivatives spontaneously solubilize the membrane bilayer. The nanodisc end product produced by this approach is similar to the conventional disc, but no detergent is used in the procedure. As a result, the solubilized membrane protein complex has maintained its native lipid environment, its native composition, and its native structure.

The presently disclosed compositions and methods can be utilized to isolate and study membrane protein complexes that are disrupted by detergent solubilization in their native form for the first time. Complexes where the interaction between the different entities is lipid or membrane mediated would appear to make particularly promising initial targets for this new technology. The technology thus opens the door for experiments that would not otherwise be possible using existing tools. It is anticipated that new membrane complexes and/or additional native components of known complexes will be discovered. In addition, the presently disclosed compositions and methods may sharply reduce the cost of studying membrane proteins. The cost for gentle, non-denaturing detergents is by far the largest single commodity expense in a typical membrane protein laboratory. The presently disclosed compositions and methods will the reduce cost of isolating and studying membrane proteins.

Figure 2:
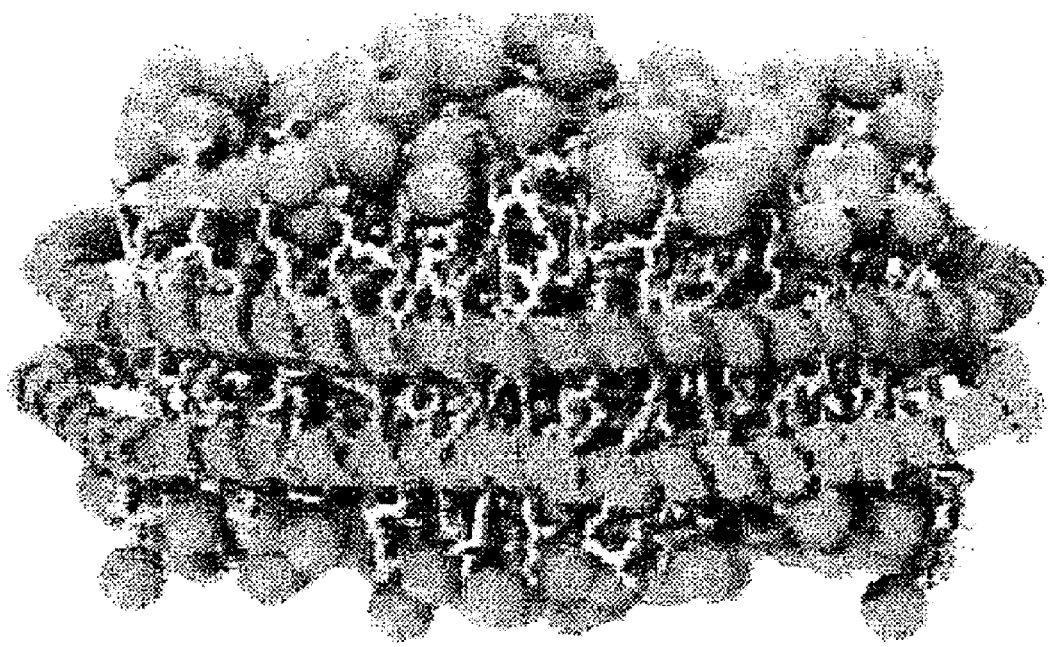
FIG. 2. illustrates that nanodiscs are stable particles with two scaffold proteins in alpha-helix conformation wrapping around a lipid bilayer.

Integral membrane proteins contain hydrophobic regions that need to interact with a detergent micelle or a model membrane system in order to prevent the protein from aggregating in aqueous solution. Model membrane systems are a particularly elegant solution for this problem because they can maintain a native lipid environment surrounding the protein. Referred to as "nanodiscs" in the literature, such membrane systems can be made from scaffold proteins derived from apolipoprotein A1 (ApoA1) to resemble naturally-occurring discoidal high-density lipoproteins (FIG. 2) (Bayburt, T. H., et. al., 2006 *Arch Biochem Biophys* 450, 215-222, the content of which is incorporated herein by reference in its entirety). (See also U.S. Pat. Nos. 7,083,958 and 7,048,949 to Sligar, which are incorporated by reference herein in their entireties). In these nanodiscs, an amphipathic scaffold protein dimerizes in such a way as to generate an amphipathic protein ring inside of which a membrane bilayer can form. If this bilayer fragment is sufficiently large, membrane proteins can reside inside the fragment and be exposed to an essentially native micro-environment. However, current technology requires that the assembly of the nanodisc membrane protein proceed via a detergent-solubilized intermediary, thus stripping the membrane protein from its native lipids and potentially destroying labile components of membrane complexes.

Figure 3:
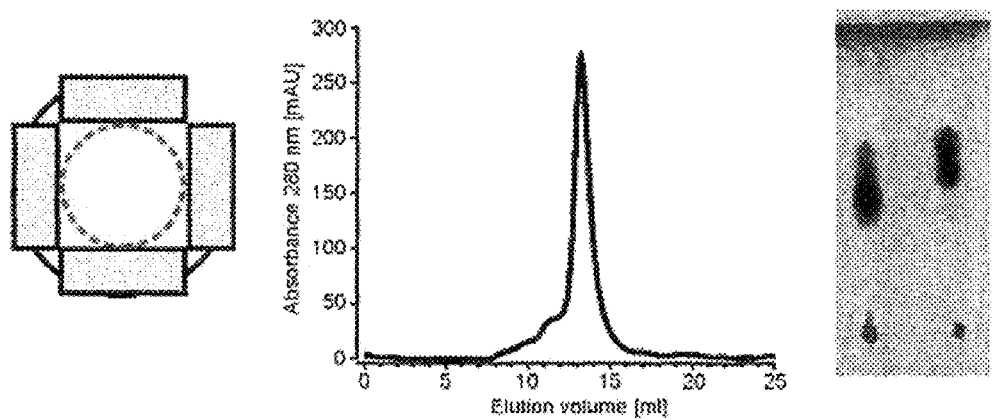
FIG. 3. illustrates production of empty LP4 scaffolding protein. Left: an amphipathic α-helical fragment of apolipoprotein A1 was repeated four times to produce the LP4 construct. Middle: gel filtration of LP4 on Superdex 200. Right: a TLC analysis of the peak (left lane) reveals the presence of native E. coli lipids. The right lane is a lipid standard.

In some embodiments, the presently disclosed compositions comprise a distinct form of polypeptides that are specifically engineered to spontaneously solubilize membrane proteins without a detergent intermediary (i.e., "LP" molecules). This is achieved by constructing polypeptides that are derivatives of scaffolding proteins (e.g., derivatives of the scaffolding proteins having N-terminal truncations, C-terminal truncations, or both) that do not exhibit a structural transition between the apo-forms and holo-forms of the scaffolding protein from which the polypeptides are derived and thus become trapped in the membrane-bound halo-form. For example, in some embodiments the polypeptides comprise multiple repeats of an amphipathic helical fragment of ApoA1. In one embodiment, the polypeptide comprises four identical repeats of an amphipathic helical fragment of ApoA1 and is referred to as "LP4." This polypeptide, LP4, was observed to be easily expressed, monodisperse, and capable of extracting native lipids when expressed in *E. coli* (FIG. 3). As shown in FIG. 3, histidine-tagged LP4 (FIG. 3, left panel) over-expressed in *E. coli*, and purified on a metal affinity column in the absence of detergent. The eluted protein was run on a gel filtration column (Superdex 200, FIG. 3, middle panel). A single main peak was observed at 13.2 ml, and the peak was analyzed by TLC (FIG. 3, right panel). The protein behaved as expected: it self-assembled as a dimer of appropriate size (as in FIG. 2) and solubilized a membrane fragment.

This polypeptide, LP4, also was observed to solubilize the KcsA potassium channel in the absence of detergent. The KcsA potassium channel is an ideal model membrane protein because it can be expressed in large quantities in *E. coli*. High expression levels are advantageous for the experiment because LP4 presumably engulfs random membrane fragments. If the density of KcsA in the membrane is high, then the probability of LP4 engulfing KcsA is also high. Initially, the KcsA1-LP4 complex was co-expressed with LP4 using a bi-cistronic expression plasmid containing both genes.

Figure 4:
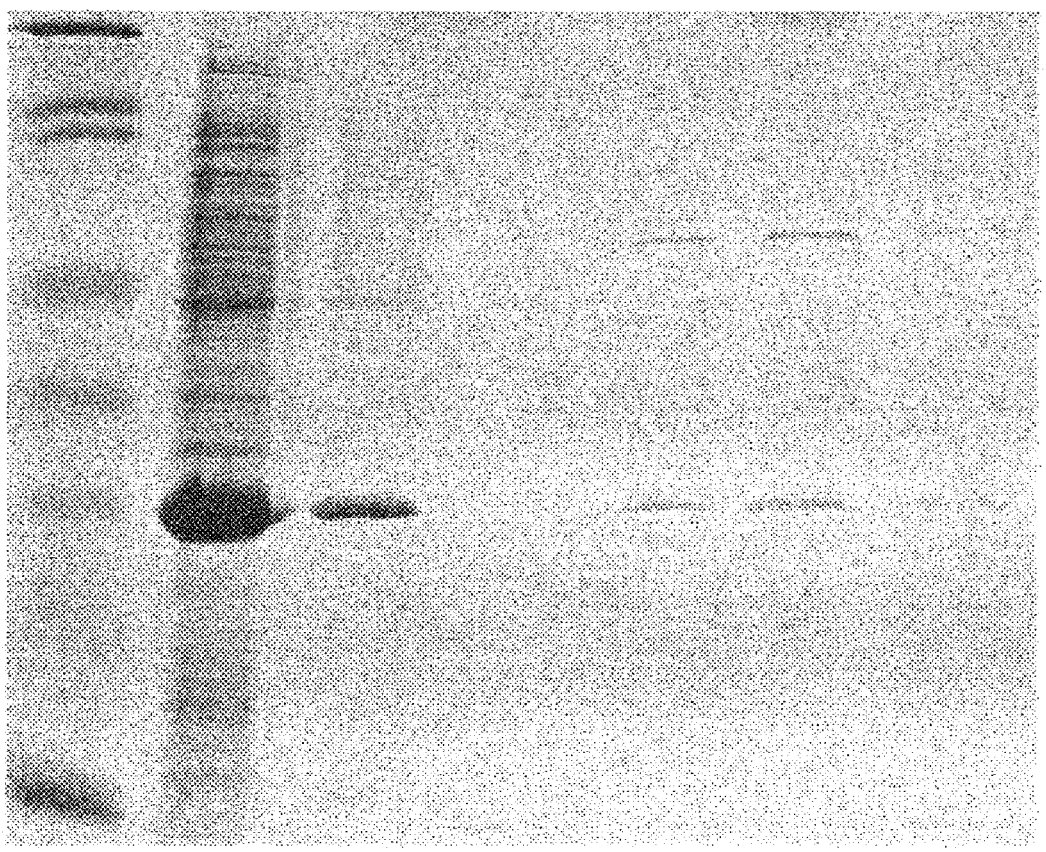
FIG. 4. illustrates an SDS-PAGE gel of LP4 (without histidine-tag) and KcsA (with histidine-tag) after co-expression in E. coli. The lanes are (from left to right): marker, flow-through, wash 1, wash 2, elution 1, elution 2, elution 3. Two proteins are co-purified: KcsA (~50 kDa) and LP4 (~25 kDa).

LP4 was expressed without a histidine-tag and KcsA was expressed with a histidine-tag in *E. coli* using a bi-cistronic construct. The LP4-KcsA complex was purified in the absence of any detergent on a metal-affinity column. A SDS-PAGE gel of the purification is shown in FIG. 4. For purification of the complex, the histidine tag was removed from LP4 and transferred to KcsA, ensuring that only KcsA, and anything that co-purifies with it, is retained on the metal-affinity column. Empty nanodiscs, expected to be the predominant species, are thus not retained. FIG. 4 demonstrates that the KcsA1-LP4 complex is indeed formed spontaneously using this approach and can be purified to near homogeneity in a single chromatography step. As expected, the SDS present in the gel destroys the KcsA1-LP4 complex by solubilizing the two proteins separately. This property demonstrates the approximate equimolar composition of the complex. In other words, a unique KcsA1-LP stoichiometry appears to exist in these nanodiscs. The data thus demonstrate that LP4 is indeed sufficient to solubilize KcsA. It is also necessary because KcsA without LP4 cannot be purified in any amount in the absence of detergent (data not shown). Also, purifying the KcsA1-LP4 complex in the presence of decylmaltoside yields only KcsA, but no LP4 (data not shown). All data are thus consistent and demonstrate that the system is functioning as expected.

Figure 5:
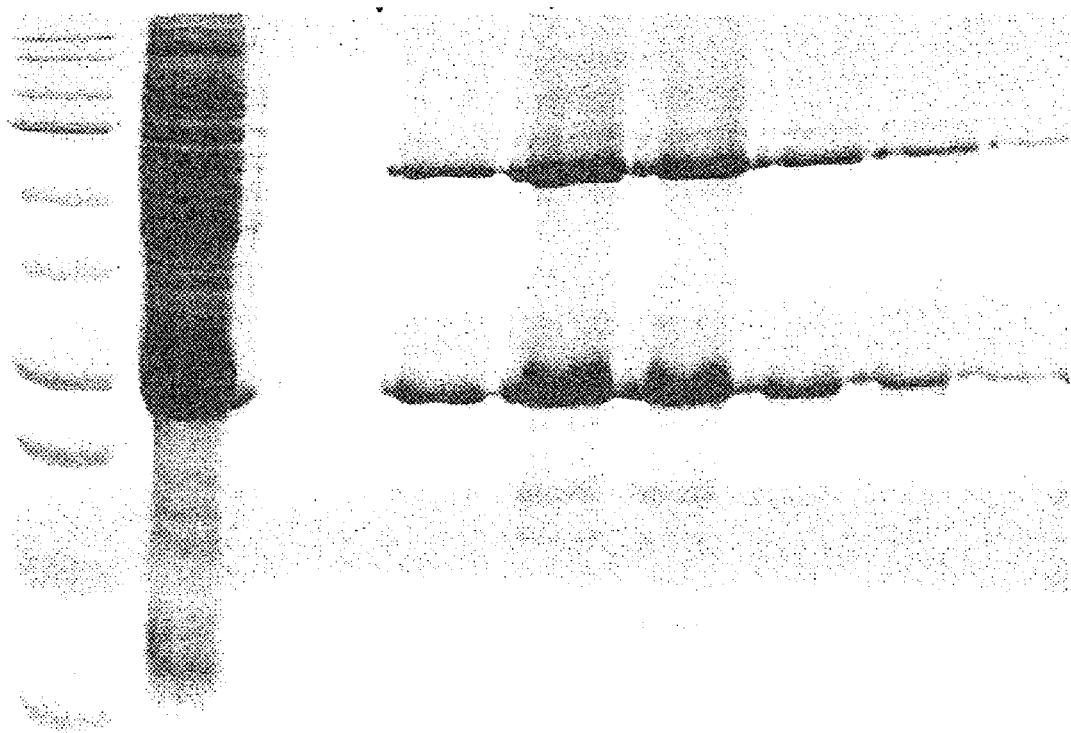
FIG. 5. illustrates an SDS-PAGE gel of LP4 (without histidine-tag) and KcsA (with histidine-tag) after separate expression in E. coli and mixing. The lanes are (from left to right): marker, flow-through, wash 1, wash 2, elutions 1-6. Two proteins are co-purified: KcsA (~50 kDa) and LP4 (~25 kDa).

In some embodiments of the presently disclosed methods, a membrane protein is expressed, and a polypeptide for solubilizing the membrane protein (as disclosed herein) is separately expressed (i.e., an "LP" molecule. The membrane protein and LP molecule are then combined. FIG. 5 demonstrates that this alternative approach for the isolation of the KcsA1-LP4 complex using separately expressed LP4 also was successful. LP4 without a histidine-tag and KcsA with a histidine-tag were expressed separately in *E. coli*. The two cell pastes were mixed and the LP4-KcsA complex was purified in the absence of any detergent on a metal-affinity column. A SDS-PAGE gel of the purification is shown in FIG. 5. The results from the separate protein expression are essentially identical to those from the co-expression studies shown in FIG. 4. These results suggest that LP4 is directed into inclusion bodies during biosynthesis and spontaneously re-folds in the presence of membrane fragments during sonication. Given the substantial practical advantages of the separate expression approach, bi-cistronic co-expression may not be a preferred method.

Figure 6:
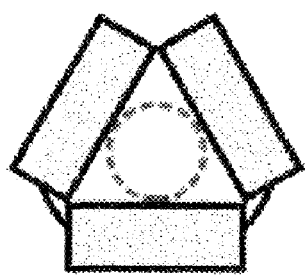
FIG. 6. illustrates nanodiscs of different size. LP(n) consisting of concatenated (n=3, 4, 5, 6) helical fragments. Where determined, the elution volumes of the empty discs on Superdex 200 are indicated below the schematic.
Figure 6:
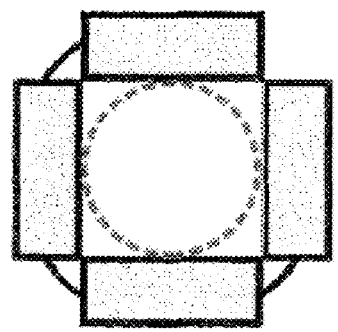
Figure 6:
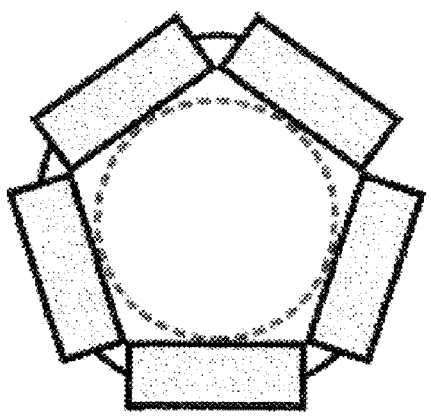
Figure 6:
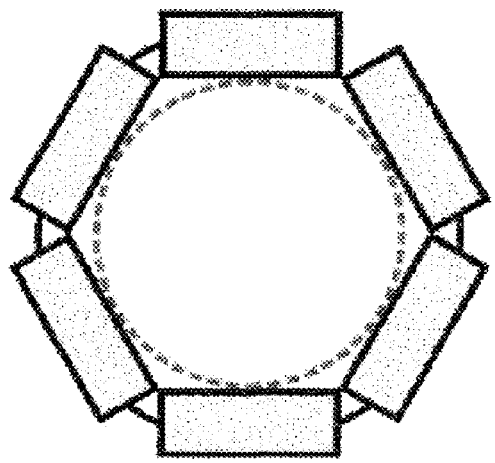

Because membrane proteins and membrane protein complexes may vary in shape and size, it may be useful to generate a family of different LP genes comprising different numbers of tandem repeats of an amphipathic helix. FIG. 6 illustrates one strategy to alter the size of the nanodisc. The constructs were prepared by shortening LP4 by one tandem repeat (LP3) or by inserting one (LP5) or two (LP6) tandem repeats into the LP4 gene. If the constructs behave as expected, then the nanodisc size should increase with increasing number of tandem repeats. For this sizing experiment, a histidine-tag was again added to all LPs in order to purify the empty discs. FIG. 6 shows that the elution volume of the main nanodisc peak shifts leftward with increasing tandem repeat number, indicating that the disc increases in size as the number of tandem repeats is increased. Using these different constructs it should now be possible to solubilize membrane proteins of different size.

Figure 7:
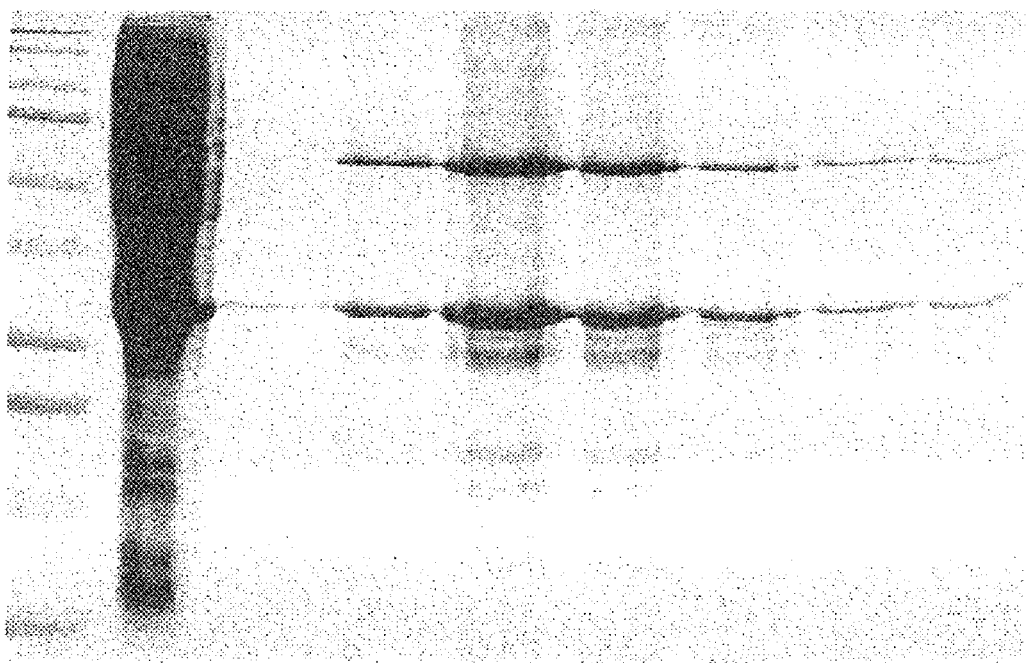
FIG. 7. illustrates an SDS-PAGE gel of LP5 (without histidine-tag) and KcsA (with histidine-tag) after separate expression in E. coli and mixing. The lanes are (from left to right): marker, flow-through, wash 1, wash 2, elutions 1-6. Two proteins are co-purified: KcsA (~50 kDa) and LP5 (~30 kDa).

These three new LPs (LP3, LP5, and LP6) were tested for their ability to solubilize KcsA. FIG. 7 demonstrates that LP5 is indeed capable of solubilizing the KcsA channel in the absence of detergent. LP5 without a histidine-tag and KcsA with a histidine-tag were expressed separately in *E. coli*. The two cell pastes were mixed and the LP5-KcsA complex was purified in the absence of any detergent on a metal-affinity column. A SDS-PAGE gel of the purification is shown in FIG. 7. As expected, the LP band in FIG. 7 exhibited a larger size than the LP band in FIG. 5. Similar results were obtained with LP6 (data not shown). All LPs with four or more elements are thus capable of solubilizing KcsA. LP3, however, was not found to be efficient at solubilizing KcsA.

In summary, the data shown here demonstrate that LPs can be constructed to spontaneously solubilize KcsA and that these LP-KcsA complexes can be purified to near homogeneity in a single chromatographic step. The general feasibility of protein-based solubilization of membrane proteins has thus been demonstrated.

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

---

I claim:

1. A polypeptide comprising multiple repeats of the full-length amino acid sequence of SEQ ID NO:1 as represented by the formula: (SEQ ID NO:1)$_n$, wherein n is 3-6.

2. The polypeptide of claim 1, wherein n is 3.

3. The polypeptide of claim 1, wherein n is 4.

4. The polypeptide of claim 1, wherein n is 5.

5. The polypeptide of claim 1, wherein n is 6.

6. The polypeptide of claim 1, as represented by the formula: N$_{ter}$-(SEQ ID NO:1)$_n$, wherein N$_{ter}$ is an amino acid sequence comprising a stretch of at least six histidine residues.

7. The polypeptide of claim 6, wherein N$_{ter}$ further comprises a protease recognition sequence that is positioned C-terminal to the stretch of histidine residues.

8. The polypeptide of claim 1, comprising SEQ ID NO:3.

9. A polypeptide comprising multiple repeats of a lipoprotein (LP) amino acid sequence as represented by the formula: (LP)$_n$, wherein n is 3-6 and LP is an amino acid sequence having at least about 95% sequence identity to the full-length amino acid sequence of SEQ ID NO:1 and the polypeptide forms a holo-form nanodisc.

10. The polypeptide of claim 9, wherein n is 4.

11. The polypeptide of claim 9, wherein n is 5.

12. A method comprising:
(a) reacting a mixture comprising:
(1) a membrane protein present in a membrane; and
(2) the polypeptide of claim 1; and
(b) isolating the membrane protein from the membrane.

13. The method of claim 12, wherein the mixture does not comprise detergent.

14. The method of claim 12, wherein the mixture does not comprise a nonionic detergent.

15. The method of claim 12, wherein the membrane comprises phospholipids.

16. The method of claim 12, wherein the membrane is a phospholipid bilayer.

* * * * *